United States Patent [19]
Nobles

[11] Patent Number: 5,820,631
[45] Date of Patent: Oct. 13, 1998

[54] DEVICE AND METHOD FOR SUTURING TISSUE ADJACENT TO A BLOOD VESSEL

[75] Inventor: Anthony A. Nobles, Fountain Valley, Calif.

[73] Assignee: NR Medical, Inc., Fountain Valley, Calif.

[21] Appl. No.: 686,201

[22] Filed: Aug. 1, 1996

[51] Int. Cl.$^6$ .................................................. A61B 17/08
[52] U.S. Cl. .......................... 606/213; 606/139; 606/144; 606/148; 606/216
[58] Field of Search ................................. 6006/213, 216, 6006/224, 139, 144, 148; 112/169, 470.11

[56] References Cited

U.S. PATENT DOCUMENTS

| | | | |
|---|---|---|---|
| 4,204,541 | 5/1980 | Kapitanov | 128/334 |
| 4,641,652 | 2/1987 | Hutterer et al. | 128/334 |
| 5,152,769 | 10/1992 | Baber | 606/145 |
| 5,201,760 | 4/1993 | West | 606/226 |
| 5,269,791 | 12/1993 | Mayzels et al. | 606/148 |
| 5,520,703 | 5/1996 | Essig et al. | 606/148 |
| 5,562,685 | 10/1996 | Mollenauer et al. | 606/144 |

*Primary Examiner*—Michael Buiz
*Assistant Examiner*—Tina T. D. Pham
*Attorney, Agent, or Firm*—Knobbe, Martens, Olson & Bear, LLP

[57] ABSTRACT

A suturing device comprises a rod with a spring needle attached to an insertion end thereof. The spring needle is housed inside of an outer guide tube for insertion into an opening in biological tissue to be sutured. After the spring needle is deployed from the outer guide tube, the rod and hence the coiled spring are then rotated to thread the spring needle up through the biological tissue to the surface. The suturing device is then removed leaving a suture in place. The method of using the device comprises introducing the compressed spring needle with a suture attached thereto into the opening in the biological tissue. An operator then rotates the spring needle to thread the spring needle to the surface of the biological tissue. After removing the spring needle the suture is tied.

5 Claims, 4 Drawing Sheets

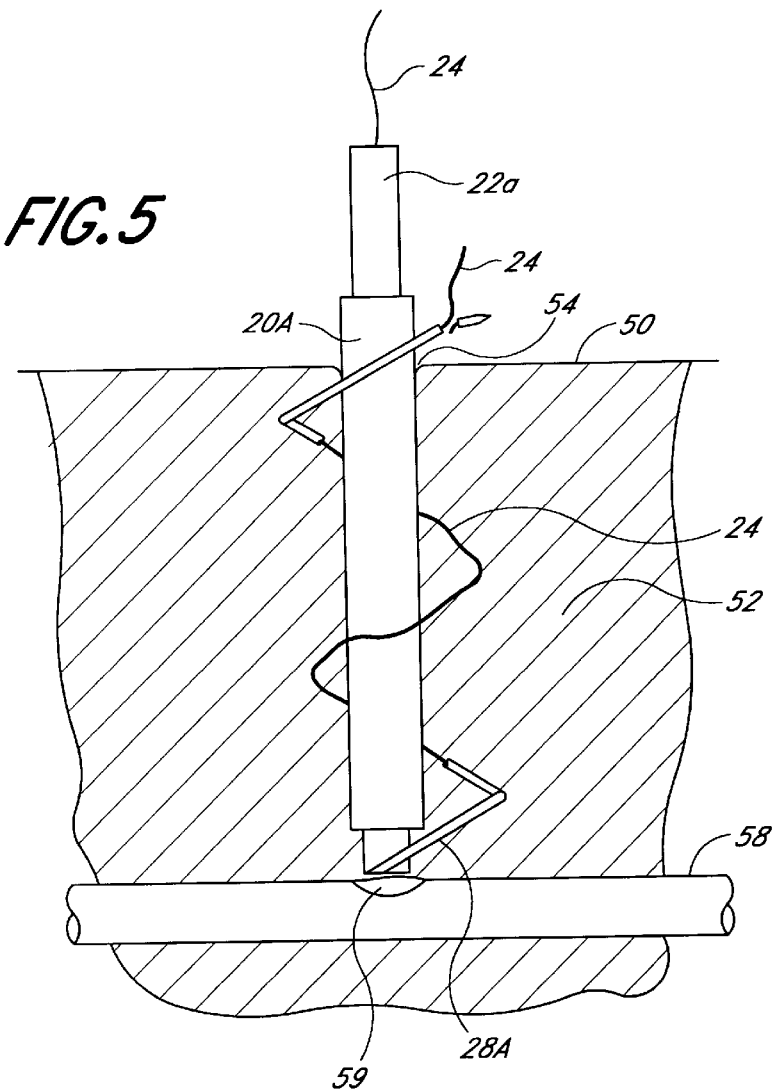
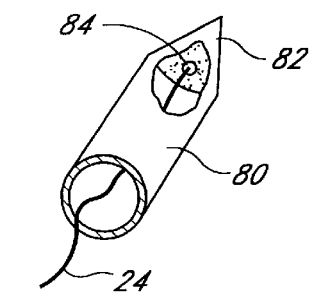
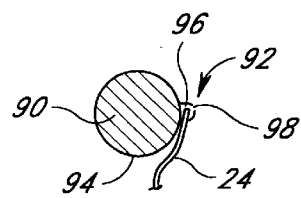
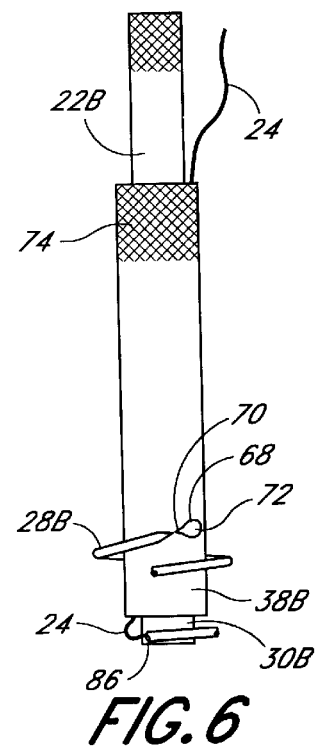
FIG. 5
FIG. 7
FIG. 8
FIG. 6

DEVICE AND METHOD FOR SUTURING TISSUE ADJACENT TO A BLOOD VESSEL

BACKGROUND OF THE INVENTION

This invention relates to devices and methods for aiding the creation of a thrombus patch.

Frequently, blood vessels in the body are punctured or cut open by accident or purposefully to perform a medical procedure such as cardiac catherization, angiography, etc. In order for a blood vessel to stop bleeding, the blood must clot creating a thrombus patch (fibrous clot) in the opening of the vessel. With the thrombus patch formed, the vessel wall begins to form scar tissue over the opening thereby closing the opening in the vessel wall.

To aid formation of a thrombus patch, direct pressure can be applied to the vessel to slow the blood flow making it easier for the thrombus patch to form. To further aid formation of a thrombus patch, the vessel can be sutured. However, if the incision is made, for example, to catherize the vessel, there is only a small opening in the flesh which is too small to allow entry and manipulation of a hemostat and conventional suturing needle. In order to suture the vessel, the opening would have to be cut further open. This is undesirable, and in the case of catherization, destroys one benefit of the catherization process, namely, gaining access to the artery through a small opening in the flesh.

As the information obtainable from and the procedures performed by cardiac catheters increase, and because the femoral artery is frequently used to gain access to an arterial pathway to the heart and other areas of the body, the frequency of incisions made in the femoral artery is increasing. Because the femoral artery cannot be sutured by conventional methods without making a large incision, direct pressure is applied for an extended period of time to aid formation of a thrombus patch. Because the femoral artery must not by completely blocked (occluded) by the direct pressure, a doctor performing the procedure applies direct pressure with a hand for the first twenty minutes after the procedure, so that the pulse can be felt to assure the artery is not occluded. After twenty minutes, the doctor turns the task of applying direct pressure over to another professional who will use large sand bags or other devices to apply direct pressure for about twenty-four (24) hours. The high pressure in the artery frequently bursts the thrombus patch requiring the process to start over again. Because thrombus patches frequently burst, a patient undergoing the procedure must remain in the hospital or catheter lab overnight for observation. This is obviously an expensive requirement because the procedures must be performed on an inpatient basis. Further, if a thrombus patch cannot be formed, a large incision must be made and the artery sutured with conventional means.

Thus, reducing the time which direct pressure must be applied to an arterial opening, the frequency with which clots on arterial vessels rupture, and the time which must be spent in the hospital, are desirable to reduce medical costs and patient discomfort.

BRIEF SUMMARY OF THE INVENTION

There is therefore provided in the practice of this invention a novel suturing device comprising an elongated member with an insertion end and a handle end. A sharp-ended spring needle with at least one coil circles an axis of the elongated member near to the insertion end. The spring needle has a holding means at its sharp end for holding a suture.

In a preferred embodiment the spring needle comprises an attached end removably connected to the insertion end of the elongated member. The preferred embodiment further comprises an outer guide tube with a means for connection to the sharp end of the spring needle, and the holding means comprises a crimped connection. The outer guide tube deployably houses the elongated member and spring needle for insertion into an opening in biological tissue to be closed. Further, the outer guide tube can be rotated to remove the spring needle. The outer guide tube is also provided with a retraction guideway for retracting the spring needle into the outer guide tube, and the outer guide tube can be provided with a deployment opening and a retraction opening for performing self explanatory functions. Preferably the retraction opening has a tear drop shape.

The spring needle is hollow in one embodiment for receiving a suture therethrough, and in another embodiment, the spring needle is solid with an external channel for receiving a suture therethrough. The spring needle is coiled so that counterclockwise rotation threads the sharp end of the spring needle outwardly toward the surface biological tissue being sutured. An at rest length of the spring needle is long enough to extend from a vessel to a surface of the biological tissue surrounding the vessel.

In another embodiment of the invention, there is provided a novel method for establishing a thrombus patch on a vessel by suturing adjacent biological tissue. A spring needle with a suture attached thereto is introduced into biological tissue to be sutured. The spring needle is rotated to thread the spring needle and attached suture toward a surface of the biological tissue. The spring needle is then removed from the opening and the suture is tied.

In a preferred embodiment of the method, the vessel is occluded upstream from the opening in the biological tissue and removing the spring needle comprises rotating the spring needle to thread the spring needle out of the biological tissue. In an alternate embodiment, the method further comprises deploying the spring needle from a hollow member, and removing the spring needle comprises retracting the spring needle into the hollow member.

These and other features and advantages of the present invention will appear from the following Detailed Description and the accompanying drawings in which similar reference characters denote similar elements throughout the several views.

BRIEF DESCRIPTION OF THE DRAWINGS

FIG. 5 is a schematic plan view of the suturing device of FIG. 3 with the spring needle deployed and threaded upwardly through biological tissue;

FIG. 6 is a schematic plan view of an alternate embodiment of a suturing device having a retraction opening;

FIG. 7 is an enlarged perspective view taken along line 7—7 of FIG. 2 of a sharp end of the spring needle; and FIG. 8 is a cross-sectional view of a solid spring needle having an external channel on its outer surface for receiving a suture.

DETAILED DESCRIPTION

Figure 1:
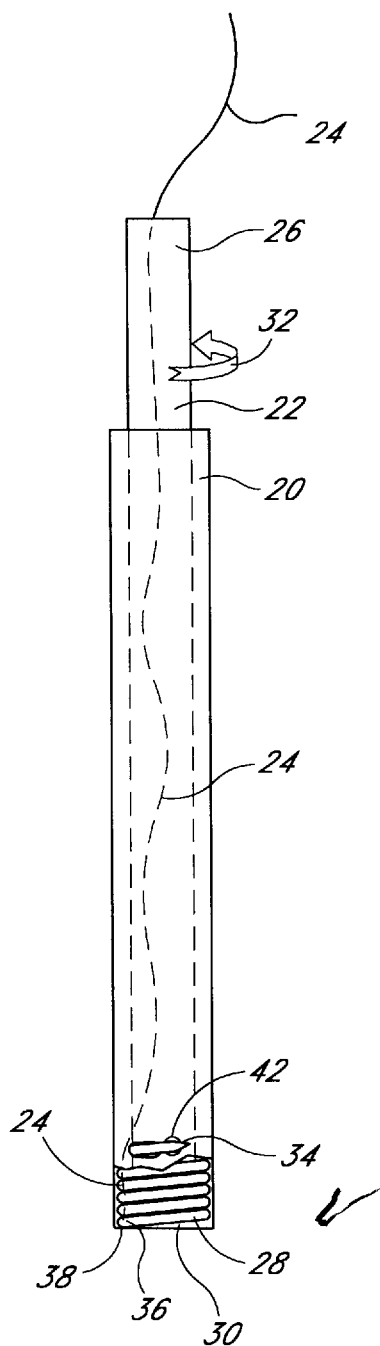
FIG. 1 is a schematic plan view of a suturing device with a spring needle housed inside of an outer guide tube.

FIG. 1, shows a preferred embodiment of a suturing device with a hollow outer guide tube 20 having an elongated member 22 extending therethrough. A suture 24 projects from a handle end 26 of the elongated member and extends through the elongated member to a spring needle 28 at the insertion end 30 of the elongated member. The suture extends through the spring needle to its end 34. The spring needle has at least one coil circling an axis, preferably a central axis, of the elongated member in proximity to the insertion end. By rotating the elongated member in a counter clockwise direction as illustrated by arrow 32, the spring needle is longitudinally expanded and threaded outwardly through the flesh to be sutured, shown upwardly in FIG. 2, creating a spiral suturing pattern. After the sharp end 34 of the spring needle protrudes from a surface 50 of biological tissue 52 being sutured, as shown in FIG. 5, the suturing device is removed as described below, and the suture is pulled tight and tied to close the opening 54 in the biological tissue.

Figure 2:
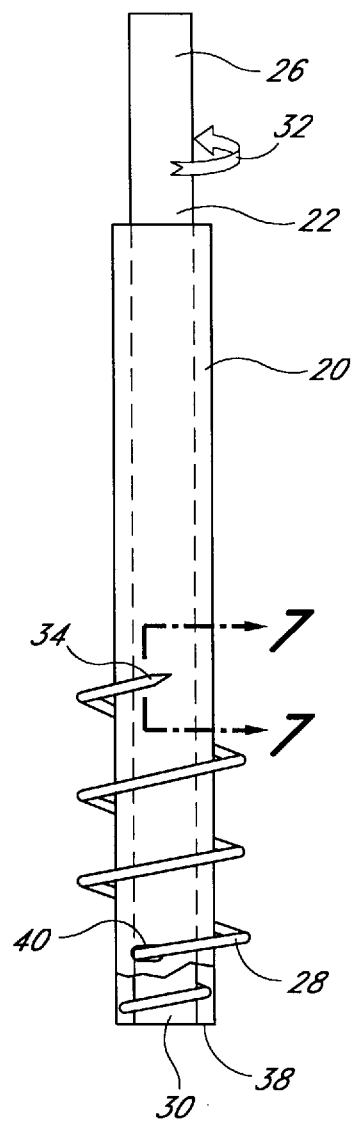
FIG. 2 is a schematic plan view of the suturing device of FIG. 1 with the spring needle partially deployed.

In the embodiment illustrated in FIGS. 1 and 2, the elongated member or rod 22 is preferably cylindrical and hollow. The aperture of the hollow rod provides a passageway for the suture to extend through to the spring needle. An independent lumen may also be provided for the suture. The rod is longer than the outer guide tube, so that the handle end 26, which is proximal to an operator, projects out of the outer guide tube, and the handle is accessible for rotation. The spring needle has an attached end 36 that is attached to the insertion end 30 of the rod with a weld or with a press fit, so that the spring needle is removable from the rod. If a weld is used to connect the spring needle to the rod, the spring needle is retracted back into the outer guide tube after the suture is in place and ready to be tightened. When the attached end of the spring needle is press fit into rod, the spring needle is pulled from the rod by rotating it relative to the rod, and the spring needle is further rotated to thread the spring needle out of the biological tissue. The press fit does not create a chance of the spring needle coming loose during suturing because the force on the needle during suturing tends to push it into the press fitting.

The outer guide tube 20, which is a hollow member, serves as what would commonly be referred to as a guide cannula or introducer. As a guide cannula, it deployably houses the spring needle. Because of the different means for deploying the spring needle, the distal end, generally designated 38, of the outer guide tube may be opened or closed. A deployment opening 40 is provided through the outer wall in the proximity of the distal end of the outer guide tube, so that it is proximate to the insertion end of the rod. The sharp end of the spring needle barely protrudes from the deployment opening when it is in the housed position. The spring needle is spot welded 42 to the outer wall of the outer guide tube, so that it stays in the housed position. The weld is broken either before or after the device is inserted in the opening in the biological tissue. To deploy the spring needle, the rod is rotated relative to the outer guide tube in a counter clockwise direction. Because the spring needle is deployed from the deployment opening, the distal end is closed in this embodiment if desired. To remove the spring needle from the biological tissue, the rod is rotated relative to the outer guide tube in a clockwise direction until the spring needle is entirely inside the outer guide tube thus retracting the spring needle. Alternatively, the spring needle is detached from the elongated member and rotated to thread it all the way out of the flesh.

Figure 3A:
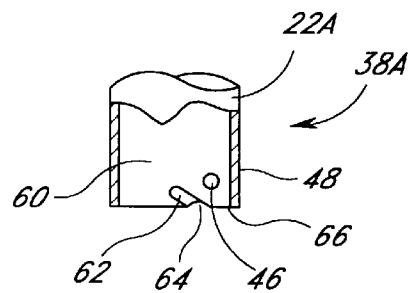
FIG. 3A is a fragmentary view in partial cross-section of a distal end of the outer guide tube of FIG. 3.
Figure 3:
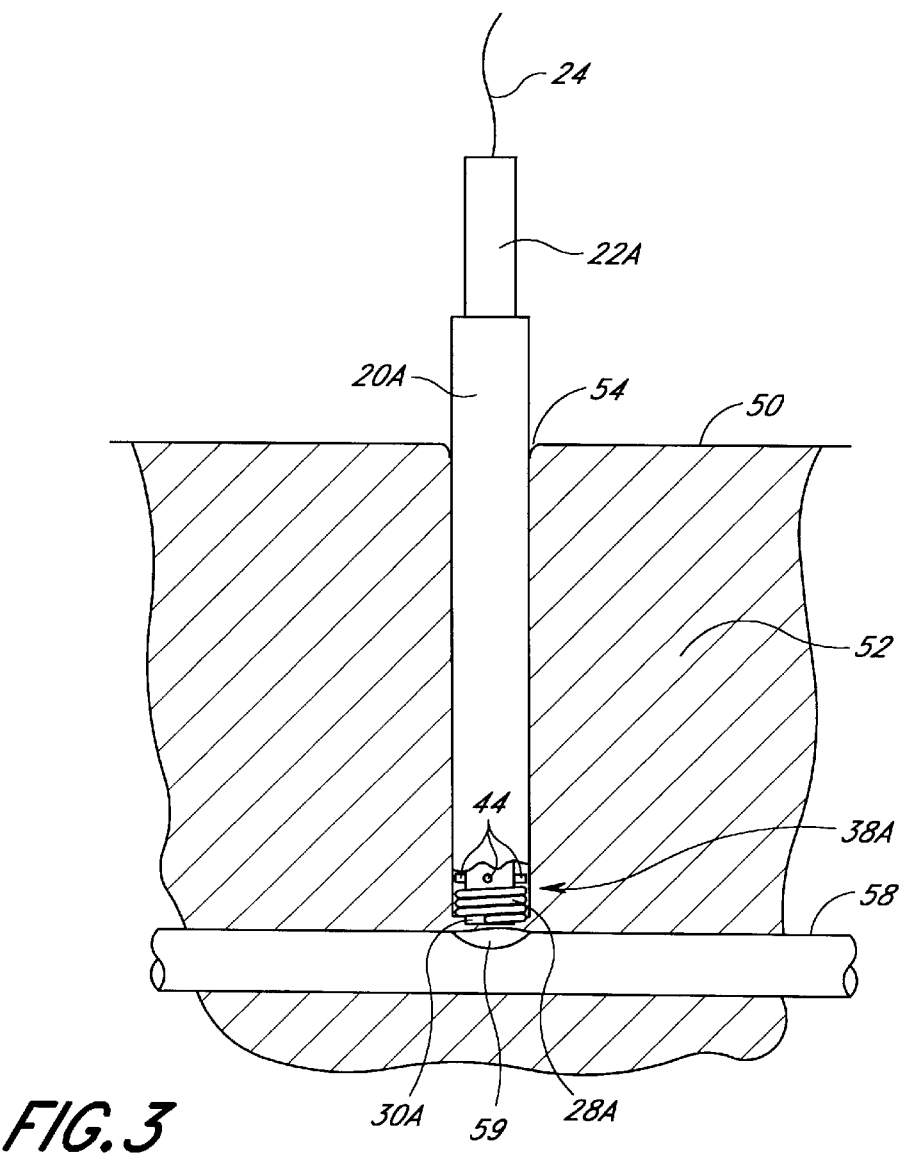
FIG. 3 is a schematic plan view of an alternate embodiment of a suturing device inserted into an opening in biological tissue and having a spring needle housed inside of an outer guide tube.
Figure 4:
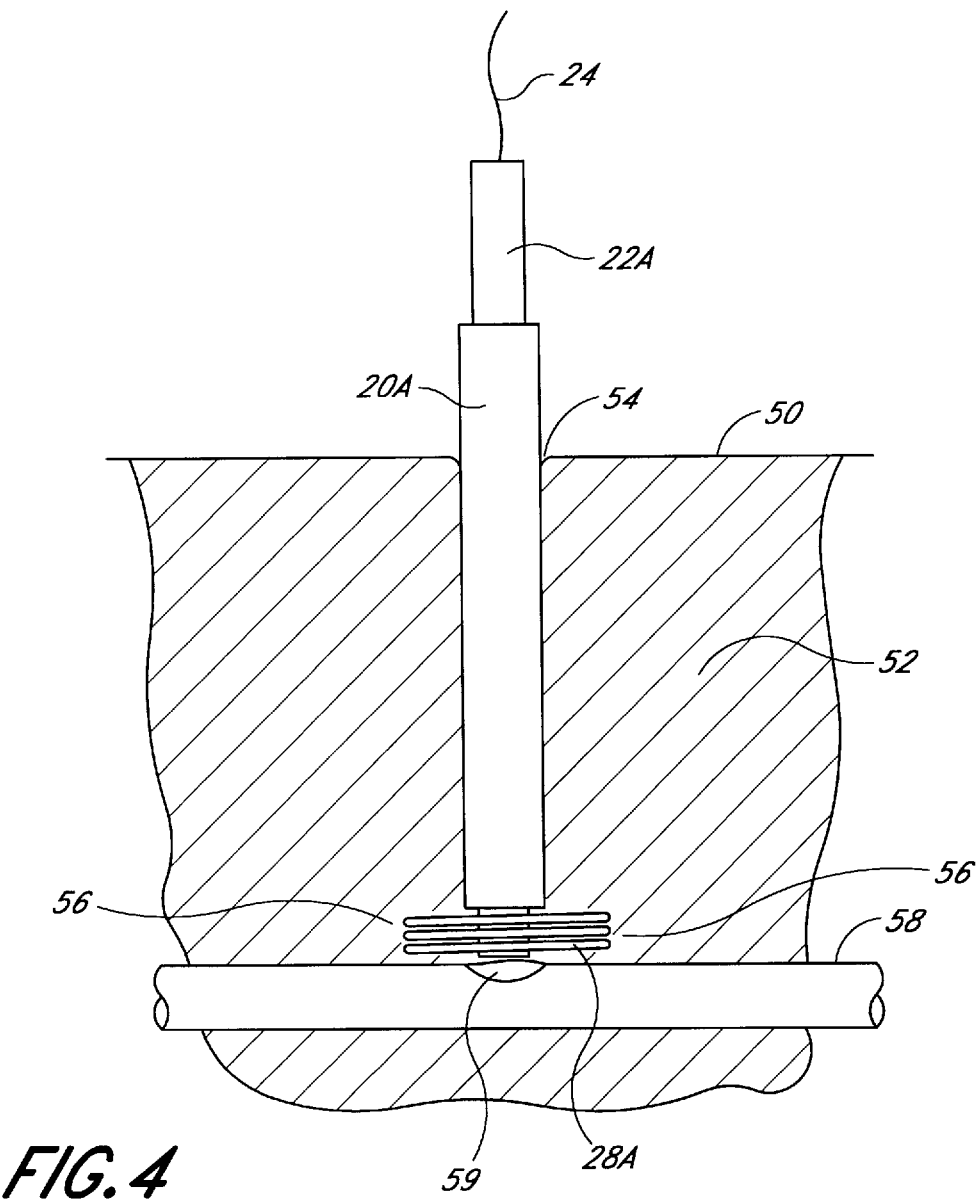
FIG. 4 is a schematic plan view of the suturing device of FIG. 3 with the spring needle deployed.

An alternate embodiment of the suturing device shown in FIG. 3 comprises an outer guide tube 20A and an internal rod 22A. The spring needle 28A is deployably housed inside the outer guide tube. The rod is provided with pins 44 around the circumference of the rod near the insertion end 30A. Alternatively, the pins are replaced by an annular ring. The pins prevent the spring needle from expanding upwardly in the outer guide tube. To deploy the spring needle, the outer guide tube is retracted and the spring is allowed to expand radially outward as illustrated in FIG. 4. The surrounding flesh 56 is compressed preventing the spring needle from expanding significantly in the longitudinal direction. Thus, the pins function to keep the spring needle compressed in the longitudinal direction until the outer guide tube is retraced and the surrounding flesh prevents longitudinal expansion. Therefore, the spring needle cannot expand longitudinally to the position shown in FIG. 5 until the rod is rotated.

In this embodiment, where the spring needle is press fit into the rod, the spring needle is preferably removed from the rod by connecting it to the distal end of the outer guide tube which has been completely retracted from the opening in the flesh. Then, the outer guide tube and the spring needle connected thereto, are rotated to thread the spring needle out of the biological tissue. Referring additionally to FIG. 3A, the distal end 38A of the cylindrical internal rod 22A has a spring needle connection aperture 46 through the outer wall 48. The aperture provides a means for connecting the sharp end 34 of the spring needle to the outer guide tube. The sharp end of the spring needle is inserted into the aperture and bent, thereby connecting the spring needle to the outer guide tube. With the spring needle connected to the outer guide tube, the outer guide tube, and hence the spring needle, are rotated in a counter clockwise direction to over come the force of the press fit and thread the spring needle out of the biological tissue.

To facilitate retracting the spring needle into the outer guide tube, the inner surface 60 of the outer guide tube defines a retraction guideway 62. The guideway comprises an angled or spiraled groove formed into the inner surface. When the spring needle is being retracted into the outer guide tube, the spring needle passes through the guideway so that its retraction is smooth. To assure that the spring needle engages the guideway during retraction, a small notch 64 is made in the bottom edge 66 of the outer guide tube at the base of the guideway. The spring needle slides across the bottom edge during retraction until it comes to the notch. The spring needle is then pulled into the notch and engages the guideway. To retract the spring needle into the distal end of the outer guide tube, the rod is turned clockwise to unthread the spring needle from the flesh. Then, the rod is pulled inside of the outer guide tube and rotated clockwise again to draw the spring needle up into the outer guide tube. Alternatively, after the spring needle is unthreaded from the flesh, the rod and spring needle could be pulled up through the outer guide tube with out rotation. This, however, is not preferred because of the chance of breaking the spring needle.

The preferred embodiment of FIG. 6 provides another means for retracting the spring needle. The outer wall of the outer guide tube 20B has a retraction opening 68 therethrough in the shape of a teardrop. The retraction opening is in proximity to the distal end 38B of the outer guide tube, so that it is located proximate to the insertion end 30B of the rod. After the suture is in place, the spring needle is retracted by rotating the rod in a clockwise direction to compress the spring needle longitudinally and unthread the spring needle from the flesh. When the spring is compressed down to the teardrop opening, the outer guide tube is pushed toward the sharp end of the spring needle until it contacts the sharp end. Then, the outer guide tube is rotated to insert the sharp end into the retraction opening.

The sharp tip 70 of the teardrop shaped opening serves as a guide to direct the sharp end toward the large portion 72 of the opening. A spot weld preferably holds the spring needle in the retracted position until it is broken just prior to suturing. The retraction opening is also used as a deployment opening. The spring needle is coiled around the outer guide tube, and the spring needle extends through the retraction opening; so that the sharp end is within the outer guide tube.

Because the rod 22B is rotated to thread the spring needle through flesh, it must withstand torsional forces. Therefore, the rod 22B is solid. If the rod is solid, the suture 24 is passed through the opening in the outer guide tube 20B to the spring needle 28B. Further, because the rod is rotated during suturing, the handle end can be knurled to help grip the rod for rotation, and the proximal end 74 of the outer guide tube is also preferably knurled because it is rotated in this and other embodiments.

The suture is brought to the surface of the flesh by the spring needle. Thus, the spring needle is provided with a means for holding a suture in proximity to the sharp end of the spring needle. FIG. 7 illustrates a hollow spring needle 80 with the suture 24 passing therethrough to the sharp end 82. The suture is crimped inside an internal opening 84 in the sharp end of the spring needle. The suture could also be tied to the sharp end of the spring needle or extend through an opening with a knot tied on its end preventing it from passing back through the opening. If the suture passes through the rod as shown in FIG. 1, the suture passes directly through the wall of the rod and into the spring needle. If the suture passes through the space between the rod and the outer guide tube, as shown in FIG. 6, the suture is introduced into the spring needle in proximity to its attached end through an opening 86. To aid initial placement of the suture in the hollow needle, the internal opening 84 is preferably conical in shape. Further, the opening through the hollow spring needle could be made just larger than the diameter of the suture, so that the suture does not have to be placed in a smaller hole for crimping.

It is also desirable for the spring needle 90 to be solid and thus rigid for some applications as shown in FIG. 8. To transport the suture 24 with a solid needle, an external channel, generally designated 92 is provided on the outer surface 94. The channel has an open center 96 larger than the diameter of the suture, so that the suture slides freely therein. The entrance 98 of the channel is smaller than the diameter of the suture, so that the suture will not come out unless it is consciously pulled out. Thus, the entrance to the channel could be closed, making a lumen external to the spring needle. However, the suture is more easily placed in the device initially if the channel has the entrance. The channel could also be provided within the circumference of the needle.

The spring needle has an at rest length long enough to extend from a vessel on which it is desirable to establish a thrombus patch to the surface of the biological tissue being sutured. The compressed coils of the spring needle may be radially layered inside the outer guide tube, so that there is one set of coils inside another. The diameter of the outer guide tube is adjusted to allow room for the two deep coils. When the spring needle expands laterally, it preferably extends approximately seven millimeters (7 mm) beyond the outer surface of the outer guide tube.

Referring back to FIGS. 3, 4, and 5 to discuss the operation of the device, the vessel 58 with the incision 59 is occluded.

The occlusion is preferably obtained with direct pressure. The rod and spring needle while housed in the outer guide tube are introduced into the opening in the biological tissue adjacent the vessel and pushed to a position next to the incision. The spring needle is then deployed as described above. After deployment, the rod and hence the spring needle are rotated in a counter clockwise direction to thread the spring needle outwardly through the flesh 52. The forces in the spring needle making it expand and the angle of the coils cause the spring needle to thread outwardly through the flesh. The direction of the coils could be reversed so that clockwise motion is required to thread the spring needle outwardly through the flesh. After the sharp end of the spring needle reaches the surface, the end of the suture attached to the sharp end is separated therefrom. To separate the suture from the hollow spring needle with the crimped connection, the sharp end is broken off exposing the suture. The suture is then cut free from the sharp end and pulled further through, so that the suture can be grasped from both ends while the device is being removed. Next the spring needle is retracted or removed as described above, and the device is removed sliding it over the suture. With the device removed, the suture is pulled tight and tied. The occluded vessel is then released. If desired, direct pressure is applied to the sutured area to further aide in formation of the thrombus patch.

Thus, a suturing device and suturing method are disclosed which utilize a spring needle to suture flesh surrounding an opening(incision) in a vessel to more quickly establish a more secure thrombus patch on the vessel and reduce patient discomfort and the patient observation time. While preferred embodiments and particular applications of this invention have been shown and described, it would be apparent to those skilled in the art that many more modifications of this invention are possible without departing from the inventive concepts herein. It is, therefore, to be understood that, within the scope of the appended claims, this invention may be practiced otherwise than as specifically described. It is, therefore, to be understood that the scope of the invention should be limited only by the appended claims, wherein what is claimed is:

What is claimed is:

1. A suturing device comprising:
    an elongated member having an insertion end and a handle end;
    a spring needle having a sharp end and at least one coil circling an axis of the elongated member in proximity to the insertion end and having an attached end removably connected to the insertion end of the elongated member;
    means for holding a suture, the holding means being provided on the spring of the needle in proximity to the sharp end; and
    an outer guide tube having a means for connection to the sharp end of the spring needle and deployably housing the elongated member for insertion into an opening in biological tissue to be closed, and the outer tube being rotatable to remove the spring needle when the sharp end of the spring needle is connected to the outer guide tube via the connection means.

2. A suturing device comprising:

an elongated member having an insertion end and a handle end;

a spring needle having a sharp end and at least one coil circling an axis of the elongated member in proximity to the insertion end and having an attached end connected to the insertion end of the elongated member;

means for holding a suture, the holding means being provided on the spring of the needle in proximity to the sharp end; and an outer guide tube having an aperture therethrough and wherein the elongated member extends through the aperture and wherein the outer guide tube comprises a deployment opening therethrough proximate to the insertion end of the elongated member, and the spring needle extends through the deployment opening so that the sharp end is outside the outer guide tube.

3. A suturing device comprising:

an elongated member having an insertion end and a handle end;

a spring needle having a sharp end and at least one coil circling an axis of the elongated member in proximity to the insertion end and having an attached end connected to the insertion end of the elongated member;

means for holding a suture, the holding means being provided on the spring of the needle in proximity to the sharp end; and an outer guide tube having an aperture therethrough and wherein the elongated member extends through the aperture and wherein the outer guide tube comprises a retraction opening therethrough proximate to the insertion end of the elongated member, and the spring needle extends through the deployment opening so that the sharp end is inside the outer guide tube in a retracted position.

4. The device according to claim 3 wherein the retraction opening comprises a teardrop shape.

5. A suturing device for aiding in establishing a thrombus patch, the device comprising:

a hollow member having a distal end and a proximal end;

a rod extending through the hollow member and having an insertion end and a handle end;

a spring needle having at least one coil, an attached end connected to the insertion end of the rod, and a sharp end; and wherein the spring needle is removably attached to the insertion end of the rod and the hollow member comprises a retractable guide cannula for holding the spring needle in a retracted position and deploying the spring needle from the retracted position when the guide cannula is retracted, and the guide cannula comprises a means for connection to the sharp end of the spring needle which is protruding from biological tissue to be sutured, and the guide cannula being rotatable to thread the spring needle out of the biological tissue.

* * * * *